United States Patent [19]

Balschmidt et al.

[11] Patent Number: 5,053,389

[45] Date of Patent: Oct. 1, 1991

[54] INSULIN PREPARATION FOR NON-PARENTERAL ADMINISTRATION

[76] Inventors: Per Balschmidt, Tibberup Alle 20, 3060 Espergrde; Finn B. Hansen, Osterbrogde 54 B, 4, 2100 Copenhagen; Bente R. Johansen, Garderhojvej 24, 2820 Gentofte, all of Denmark

[21] Appl. No.: 132,969

[22] PCT Filed: Apr. 14, 1987

[86] PCT No.: PCT/DK87/00038

§ 371 Date: Dec. 14, 1987

§ 102(e) Date: Dec. 14, 1987

[30] Foreign Application Priority Data

Apr. 18, 1986 [DK] Denmark .............................. 1792/86

[51] Int. Cl.$^5$ ............................................. A61K 37/20
[52] U.S. Cl. ..................................... 514/4; 514/3; 514/866; 530/303
[58] Field of Search ............... 514/3, 4, 866; 530/303, 530/304, 305

[56] References Cited

U.S. PATENT DOCUMENTS

| | | | |
|---|---|---|---|
| 3,868,356 | 2/1975 | Smyth | 530/303 |
| 4,153,689 | 5/1979 | Hirai et al. | 514/4 |
| 4,164,573 | 8/1979 | Galinsky | 514/3 |
| 4,442,090 | 4/1984 | Kakeya et al. | 514/784 |
| 4,534,894 | 8/1985 | Cerami et al. | 530/303 |

FOREIGN PATENT DOCUMENTS

| | | |
|---|---|---|
| 1925/83 | 4/1983 | Denmark . |
| 2294/84 | 5/1984 | Denmark . |
| 84301546.2 | 10/1984 | European Pat. Off. . |
| 84401175.9 | 12/1984 | European Pat. Off. . |
| 1527605 | 10/1978 | United Kingdom . |
| 1554157 | 10/1979 | United Kingdom . |

OTHER PUBLICATIONS

*Biol. Chem. Hoppe-Seyler*, vol. 366, pp. 521-525 (1985) by Fischer et al., entitled "A Shortened Insulin with Full in Vitro Potency".

*Hoppe-Seyler's Z. Physiol. Chem.*, vol. 356, pp. 1397-1404 (1973) by Hans-Gregor Gattner, entitled "B-Chain Shortening of Matrix-Bound Insulin . . . ".

*Eur. j. Biochem*, vol. 31, pp. 470-473 (1972) by Massey et al., entitled "The Effect of Acylation on the Molecular Size of Insulin".

*Biochemistry*, vol. 19, pp. 5926-5931 (1980) by Carpenter et al., entitled "Tetrakis (3-nitrotyrosine) Insulin".

"New Forms of Insulin" by Galloway et al., pp. 640-648.

*Diabetes*, vol. 27, No. 3, pp. 296-299 by Hirai et al., entitled "Nasal Absorpition of Insulin in Dogs".

*Proc. Natl. Acad, Sci. U.S.A.*, vol. 82, pp. 7419-8423 (11/85) by Gordon et al., entitled "Nasal Adsorpition of Insulin: Enhancement by hydrophobic Bile Salts".

*International Journal of Pharmaceutical*, pp. 173-184 (1981) by Hirai et al. entitled "Mechanisms for the Enhancement of the Nasal Adsorption of Insulin . . . ".

*Method in Enzymology*, vol. 61, pp. 125-143 (1981) by Valdes et al., entitled "(9) Study of Protein Subunit Association Equilibria by Elution Gel Chromatography".

*Primary Examiner*—F. T. Moezie

[57] ABSTRACT

Insulin preparations for non-parenteral administration and containing one or more insulins or insuling derivatives, which in solution in the physiological pH range predominantly are present as monomers, usual additives and possibly a conventional insulin and possibly one or more adsorption promoting substances provide a fast absorption of the insulin activity administered.

3 Claims, 1 Drawing Sheet

INSULIN PREPARATION FOR NON-PARENTERAL ADMINISTRATION

TECHNICAL FIELD

The present invention relates to insulin preparations for non-parenteral administration.

BACKGROUND ART

Ever since the discovery of insulin and its successive use for the treatment of Diabetes the only form of administration used in practice has been subcutaneous or intramuscular injection, generally several times a day. In spite of a rapid technical development, this administration still involves a number of disadvantages, such as pain, risk of infection as well as a possibility of chronic tissue injuries. Consequently, there has always been a wish to administer the insulin non-parenterally, and thus in particular oral, rectal, nasal, as well as ophthalmic administrations have been investigated.

The ophthalmic administration of insulin has been disclosed in the specification of Danish Patent No. 135,268, according to which specification an insulin-containing hydrogel is placed under the eyelid. Thereby an absorption of 5-20% of the amount of insulin administered is obtained over a period of several hours.

The oral administration demands that special protective measures are taken in order to prevent the insulin from being decomposed, before absorption can take place through the intestinal mucosa. This can e.g. be done as stated in the specification of Danish patent application No. 1925/83 and Danish patent application No. 2294/84, according to which enzyme inhibitors are added and an encapsulation in a bile-soluble material may be made. Oral administration only gives an absorption of 1-2% of the amount of insulin administered, cf. Galloway et al., Diabetes 21 (1971), pages 640-648.

Rectal insulin administration is disclosed in e.g. German Published Specification No. 2,641,819, U.S. Pat. No. 4,164,573 and U.S. Pat. No. 4,442,090. In this way of administration the insulin is encapsuled in the form of a suppository in which the presence of an enzyme inhibitor is normally not necessary. Hereby an absorption of the amount of insulin administered of about 5% can be obtained.

In the forms of administration mentioned above use is made in almost all cases of a surface-active additive to increase the absorption rate and efficiency of the insulin through the mucosae. An example of such absorption promoting adjuvants are polyoxy ethylene fatty alcohol ethers and in particular bile acids or salts thereof.

Such additives are particularly effective in nasal administration of insulin, vide GB Patent Specifications No. 1,527,605 and No. 1,554,157, and the technique has been further described by S. Hirai et al., Diabetes 27 (1978), pages 296-299, and G. S. Gordon et al., PNAS 82 (1985), pages 7419-7423. In this form of administration the insulin is administered in solution as drops or better in atomized form to the nasal cavity, whereafter the absorption through the nasal mucosa occurs so rapidly, that the maximum insulin concentration is obtained already after 10 to 30 minutes. This rapidly commencing absorption is of particularly therapeutical importance as the maximum insulin concentration in normal subcutaneous injection of dissolved insulin does not commence until after 30-60 minutes, which may cause problems in a much employed Diabetes therapy, in which injections of rapidly acting insulin are given immediately before the principal meals.

However, in the nasal form of administration an adverse effect on the mucosae due to the added absorption promoting adjuvants has been demonstrated after some time, vide S. Hirai et al., Int. J. Pharm. 9 (1981), pages 173-184.

This problem is said to be solved by the use of certain fusidic acid or cephalosporine derivatives as adjuvants, vide the specification of European patent application No. 128,831. The proportion of insulin absorbed by nasal administration in dissolved and atomized form is said to be up to about 20% in the publications mentioned above.

An embodiment of the nasal administration in which the use of surface-active adjuvants can be avoided is known from European patent application No. 122,036. Said embodiment consists in the administration of the insulin as a powder, whereby use is made of a water-insoluble, but water-absorbing carrier, e.g. crystalline cellulose. Hereby the particles adhere to the nasal mucosa, and moisture is absorbed which has the effect that the insulin attains an intense contact with the mucosa and thereby can be absorbed with a high efficacy.

In all the known insulin preparations for non-parenteral administration a conventional commercially available insulin is used as the basis of the formulation. When such an insulin is dissolved at physiological pH value a concentration-dependent equilibration is established between monomeric, dimeric, hexameric, and polymeric insulin. The degree of self-association can be determined e.g. by ultracentrifugation or by gel filtration methods, vide e.g. R. Valdes Jr. and G. A. Ackers, "Methods in Enzymology", Vol. 61 (Enzyme Structure, part H, edt.: Hirs & Timasheff), Academic Press 1979, pages 125-142. In conventional commercially available preparations of dissolved insulin a very large proportion of the insulin is present as hexamers.

SUMMARY OF THE INVENTION

By the use of insulins or insulin derivatives which in solution in the physiological pH range predominantly are present as monomers in insulin preparations for non-parenteral administration a still more rapid absorption of the insulin activity administered is obtained, as maximum concentration in serum is attained already after 5-10 minutes.

DISCLOSURE OF THE INVENTION

Figure 1:
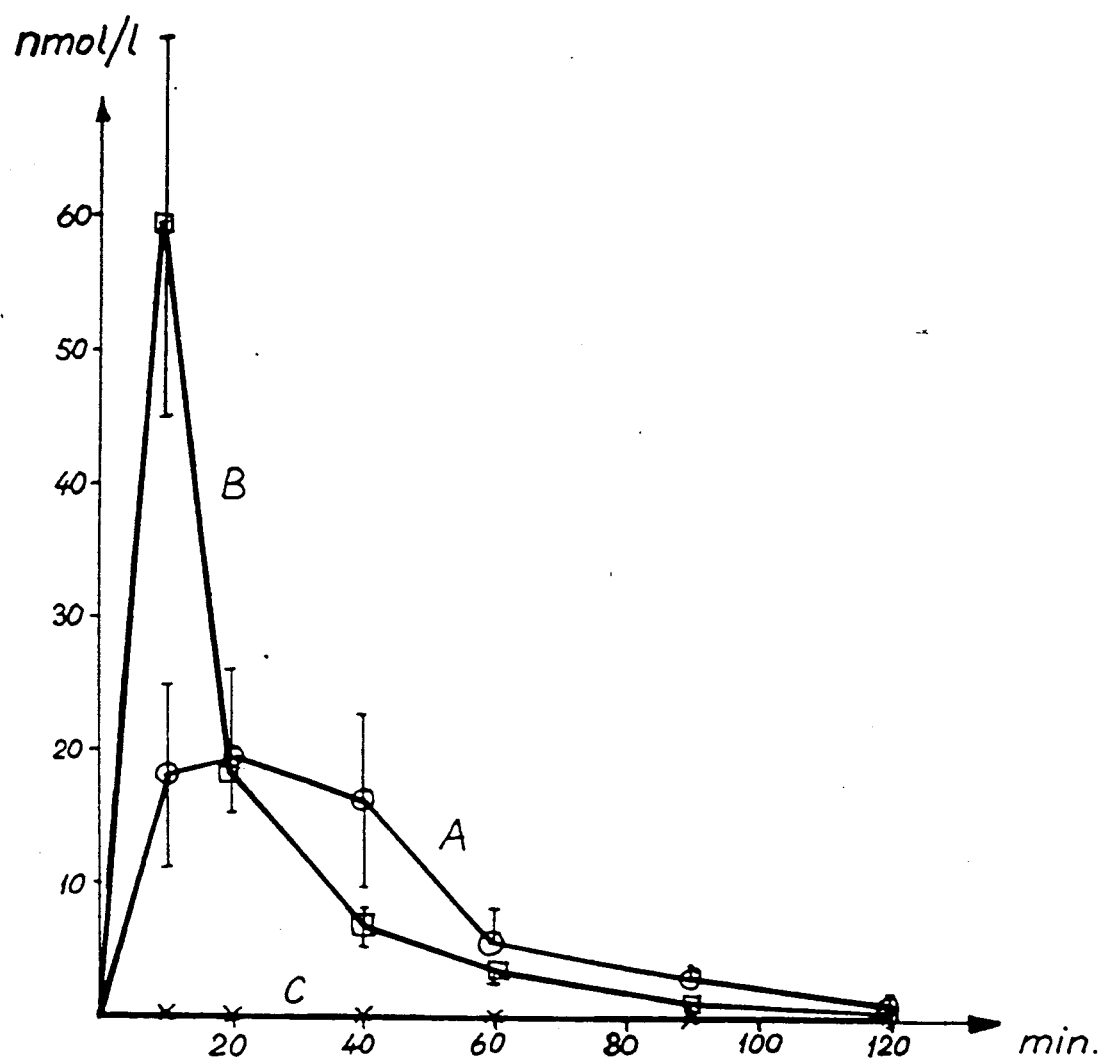
FIG. 1 depict the plasma insulin levels (means and S.E.M.) at various sampling time.

The insulin preparations of this invention are characterized in that they contain one or more insulins or insulin derivatives which in solution in the physiological pH range predominantly are present as monomers and usual additives and, possibly, a conventional insulin and, possibly, one or more absorption promoting substances. The physiological pH range comprises pH values from about 6.5 to about 8.5.

In particular, the invention relates to an insulin preparation for non-parenteral administration, which preparation as the main insulin active component contains insulin derivatives which in solution in the physiological pH range predominantly are present as monomers.

In particular, the invention relates to insulin preparations for nasal administration.

Nasal insulin preparations may e.g. be dosed from a bottle equipped with a manual atomizer designed for delivering a specific volume of insulin solution per dose. Thus, the nozzle of the bottle is led into a nostril before the atomization which may be repeated in the other nostril.

Insulins or insulin derivatives which predominantly are present as monomers often exhibit reduced insulin activity. Thus, such insulins or insulin derivatives that still exhibit a considerable insulin activity, e.g. A1,B1,B29-trisuccinyl insulin, tetrakis-(3-nitrotyrosine)-insulin as well as des-pentapeptide(B26-30)-insulin, des-pentapeptide(B26-30)-insulin-B25-amide, and sulphated or phosphorylated insulin, are useful in the preparation of the invention.

Trisuccinyl insulin can be prepared by treating insulin with succinic acid anhydride (D. E. Massey, D. G. Smyth: Eur. J. Biochem. 31 (1972), pages 470–473); tetranitro-insulin can be obtained by reaction between insulin and tetranitro methane (F. H. Carpenter et al., Biochemistry (USA) 19 (1980), pages 5926–5931); despentapeptide-insulin is formed by digesting insulin with pepsin (H. G. Gattner: Hoppe-Seylers Z. Physiol. Chem. 356 (1975), pages 1397 –1404); despeptapeptide-insulin amide can be prepared by condensing desoctapeptide insulin and gly-phe-phe-NH$_2$ by trypsin-assisted peptide bond formation (W. H. Fischer et al., Biol. Chem. Hoppe-Seyler 366 (1985), pages 521–525), and sulphated insulin may be obtained by reacting insulin with a carbodiimide in the presence of sulphuric acid (S. Pongor et al., Diabetes 32 (1983), pages 1087–1091, U.S. Pat. No. 4,534,894).

Useful absorption promoting substances are surface-active compounds, as e.g. fatty alkyl or fatty acyl substituted polyethyleneglycol, block copolymers of polyethyleneglycol and polypropyleneglycol, salts of bile acids, as e.g. taurocholic acid, deoxycholic acid and glycodeoxycholic acid, salts of N-acyl amino acids, as e.g. lauroyl sarcosine and palmitoyl glutamic acid, as well as derivatives of fusidic acid and cephalosporine. Particularly useful are such substances exhibiting the least possible tissue irritation.

Physiologically acceptable acids or bases of pH values near the physiological pH range can be used as buffers, e.g. phosphates, tris(hydroxymethyl)-aminomethane (TRIS) and glycyl glycine. Physiologically acceptable salts or polyhydroxy compounds can be used as isotonica, e.g. sodium chloride, glycerine or mannitol. Useful preserving agents comprise phenol or benzyl alcohol or similar substances being active in the physiological pH range.

Useful suppository vehicles in preparations for rectal administration are premixed synthetic fats, e.g. "Witepsol" ®, or partly decomposed vegetable oils and fats or Macrogols.

In powderous preparations for nasal administration dried water-absorbing, but water-insoluble substances, e.g. cross-linked polyvinyl pyrrolidon or in particular crystalline cellulose having a particle size between 20 and 200 μm can be used as carriers.

Aqueous preparations intended for nasal administration generally contain 40–500 I.U. insulin activity per ml, preferably ranging from 80 to 300 I.U./ml. The content of surface-active absorption promoting substances is usually in the range of from 0.1 to 10%, and a content of from 0.5 to 5% is preferred. The pH of the preparation should be near the physiological pH and a pH range between 7 and 8 is preferred.

Powders for nasal administration generally contain 0.5–10 I.U. insulin activity per mg, preferably 1–8 I.U./mg. The insulin or insulin derivative used in these preparations should be prepared as an easily water-soluble product, preferably by lyophilization from solutions having a pH of between 6.5 and 8.5.

Rectal insulin preparations in the form of suppositories generally contain 2–200 I.U. insulin activity per gram, of which 5–100 I.U./gram is preferred. The absorption promoting substance is usually added in an amount of 0.1–25% by weight, and 0.5–10% (w/w) is preferred. The preparations are generally cast as suppositories of 0.5–3 grams, preferably weighing 1–2.5 grams.

MODES FOR CARRYING OUT THE INVENTION

The invention is further illustrated by the following Examples.

EXAMPLE I

Formulation of a preparation for rectal administration 95 mg of trisuccinyl porcine insulin and 1.0 gram of sodium cholate were thoroughly mixed into 100 ml of melted "Witepsol" ® at 36° C., and the resulting mass was cast in forms to suppositories of 2 ml, each containing 20 I.U. of insulin activity.

EXAMPLE II

Formulation of a preparation for nasal administration 75 mg of des-pentapeptide(B26–30) porcine insulin-B25-amide were dissolved in 3 ml of water by means of a small amount of hydrochloric acid, whereafter 5 ml of 0.02 M sodium dihydrogen phosphate in 1% phenol were added. The pH value was adjusted to 8.5 with sodium hydroxide, and water was added until 10 ml. This solution was now mixed with 10 ml of a freshly produced 2% solution of sodium glycodeoxycholate in 0.25 M sodium chloride, adjusted to a pH value of 7.5 with hydrochloric acid and subsequently filled into a bottle, which was sealed with a manual atomizer delivering a specific volume of solution per puff. With a dosage volume of 100 μliters 10 I.U. of insulin activity was thus administered through a single puff.

EXAMPLE III

Preparation of des-pentapeptide(B26–30) porcine insulin-B25-amide 500 mg of des-octapeptide(B23–30) porcine insulin prepared in a manner known per se by trypsin digestion of porcine insulin and 1000 mg of gly-phe-phe-NH$_2$ prepared in a manner known per se by Merrifield-synthesis were dissolved in a mixture of 6 ml of dimethylformamide and 3 ml of water, and the pH value was adjusted to 6.5 with triethylamine or acetic acid. A solution of 25 mg trypsin in 500 μliters of 0.001 M calcium acetate was added with stirring, and the reaction mixture was left at 20° C. for 4 hours. Then the proteins were precipitated from the solution by the addition of 100 ml of acetone and separated by centrifugation. The precipitate was redissolved in 20 ml of 1 M acetic acid, 7 M urea and gel-filtered on a 5×85 cm column of "Sephadex" ® G 50 Superfine in 1 M acetic acid. The fractions containing the protein main fraction were collected and freeze-dried.

The freeze-dried protein was redissolved in 40 ml of 7 M urea, the pH value being adjusted to 8.1 with 1 M TRIS and applied to a 2.6×20 cm column of DEAE-cellulose ("Whatman"® DE-52) packed and equilibrated in 0.02 M TRIS/hydrochloric acid, 7 M urea pH value 8.1. Thereafter the column was eluted at 4° C. with a sodium chloride gradient from 0.1 M in the same buffer over 48 hours at a flow of 40 ml per hour. The fractions containing the protein main peak first eluted were collected and desalted on "Sephadex"® G 25 Fine in 1 M acetic acid. The proteinaceous pool was freeze-dried.

Yield: 260 mg of des-pentapeptide(B26-30) porcine insulin-B25-amide.

EXAMPLE IV

Preparation of trisuccinyl human insulin 250 mg of Zn-free semisynthetically prepared human insulin were dissolved in 12.5 ml of 0.5 M TRIS/acetic acid, 7 M urea pH 8.5, whereafter 25 mg of succinic anhydride were added with stirring. The mixture was left with stirring for 1 hour at 20° C. Thereafter the reaction mixture was desalted on "Sephadex"® 25 in 0.05 M ammonium hydrogen carbonate, and the proteinaceous fractions were freeze-dried. The freeze-dried substance was dissolved in 1.5 M acetic acid, 0.05 M sodium chloride, 7 M urea and applied to a 2.6×20 cm column of SP-"Sephadex"® C-25, packed and equilibrated in the same buffer. Then there was eluted with a 0.05→0.2 M sodium chloride gradient over 24 hours at a flow of 40 ml per hour at 4° C. The protein main peak first eluted was collected and desalted on "Sephadex"® G 25 in 0.05 M ammonium hydrogen carbonate. The proteinaceous eluate was freeze-dried.

Yield: 125 mg of trisuccinyl human insulin.

EXAMPLE V

Preparation of sulphated porcine insulin

250 μliters of concentrated sulphuric acid were added dropwise with stirring to 4.75 ml of ice-cold anhydrous dimethyl formamide, whereupon 100 mg of Zn-free porcine insulin were dissolved therein with continued stirring. 500 mg of dicyclohexylcarbodiimide dissolved in 1 ml of dimethyl formamide were added, and the mixture was shaken at 4° C. for 6 hours. Hereafter about 5 grams of crushed ice were added, and the mixture was neutralized with 10 N sodium hydroxide solution. 10 ml of water were added, and the precipitated dicyclohexyl urea was separated by centrifugation. Thereafter the supernatant was desalted on a "Sephadex38 ® G 25 column in 0.05 M ammonium hydrogen carbonate solution and freeze-dried.

Yield: 80 mg of sulphated porcine insulin.

EXAMPLE VI

Formulation of a preparation for nasal administration.

70 mg of sulphated porcine insulin were dissolved with stirring in 10 ml of 0.14 M of sodium chloride containing 1% of sodium-tauro-24,25-dihydro-fusidate and 0.3% m-cresol, the pH value being adjusted to 7.4. Hereby a preparation containing 150 I.U. of insulin activity per ml is obtained, which preparation is particularly suitable for administration from a spray dosage container due to the good shaking stability of the insulin derivative.

EXAMPLE VII

Formulation of a preparation for nasal administration 100 mg of des-pentapeptide (B26-30) porcine insulin-B25-amide were dissolved in 20 ml of water with the pH value being adjusted to 7.5 with sodium hydroxide, and the solution was freeze-dried. The resulting insulin powder was thoroughly mixed in a mortar with 800 mg of crystalline cellulose so as to obtain a uniform powder composition containing 3 I.U. of insulin activity per mg.

Thereafter the nasal powder can be administered to the nasal mucosa by means of an insufflator, which may be designed in such a way that the powder is administered as a dosed medicine in the form of a gelatine capsule being perforated immediately before the insufflation.

EXAMPLE VIII

In vivo experiments

Male, 6 weeks old, Wistar rats (150±5 grams) made diabetic 3 days prior by intravenous injection of streptozotocin (65 mg/kg) were anaesthetized with pentobarbital (50 mg/kg) intraperitoneally, and polythene catheters were inserted into a carotid artery for blood sampling. A tracheal cannula was inserted in the rats before the intranasal insulin administration.

Groups of 4 rats were dosed intranasally at 0 min. with 10 μliter's of one of the following preparations:

A.
 250 I.U./ml of Zn-insulin (human)
 1/75 M sodium phosphate
 1.6% (vol/vol) of glycerol
 1.0% (weight/vol) of sodium glycodeoxycholate B.
 250 I.U./ml of des-pentapeptide (B26-30) porcine insu
 lin-B25-amide
 1/75 M sodium phosphate
 1.6% (vol/vol) of glycerol
 1.0% (weight/vol) of sodium glycodeoxycholate C.
 1/75 M sodium phosphate
 1.6% (vol/vol) of glycerol
 1.0% (weight/vol) of sodium glycodeoxycholate 250 μliters of blood were sampled into heparinized ice-cold tubes at −5, 10, 20, 40, 60, 90, and 120 minutes, and the plasma samples were frozen after centrifugation for later insulin determination by radioimmunoassay.

Table I and FIG. 1 depict the plasma insulin levels (means and S.E.M.) at the various sampling times. The detection limit is 0.05 nmol/liter.

It can be seen that the monomeric des-pentapeptide insulin-amide (B) was absorbed faster and more reproducibly than the conventionally used hexameric insulin (A).

TABLE I

| Preparation | No. of rats | | Plasma insulin concentration (nmol/liter) | | | | | | |
|---|---|---|---|---|---|---|---|---|---|
| | | | \-5 | 10 | 20 | 40 | 60 | 90 | 120 |
| A (Zn-insulin) | 4 | x̄ ± S.E.M.: | <0.05 | 18.07 ± 6.81 | 18.14 ± 6.87 | 16.32 ± 6.42 | 5.97 ± 2.17 | 3.21 ± 0.99 | 1.21 ± 0.34 |
| B (DPI-amide) | 4 | x̄ ± S.E.M.: | <0.10 | 59.39 ± 14.25 | 19.46 ± 2.74 | 7.13 ± 1.83 | 3.88 ± 1.17 | 1.42 ± 0.46 | 0.96 ± 0.26 |
| C (placebo) | 4 | x̄ ± S.E.M.: | <0.05 | <0.08 | <0.07 | <0.06 | <0.15 | <0.08 | <0.09 |

We claim:

1. A method for treating diabetes in a warm-blooded animal by non-parenterally administering to said warm blooded animal an insulin preparation comprising des[(B26-30)-pentapeptide] insulin-B25-amide, an absorption promoting substance, a physiologically acceptable additive and, optionally, a conventional insulin.

2. The method according to claim 1, wherein said insulin preparation is administered nasally.

3. Insulin preparation for non-parenteral administration comprising des[(B26-30)-pentapeptide] insulin-B-25-amide, an absorption promoting substance, a physiologically acceptable additive and, optionally, a conventional insulin.

* * * * *

UNITED STATES PATENT AND TRADEMARK OFFICE
CERTIFICATE OF CORRECTION

PATENT NO. : 5,053,389

DATED : October 1, 1991

INVENTOR(S) : Per Balschmidt, Finn B. Hansen and Bente R. Johansen

It is certified that error appears in the above-identified patent and that said Letters Patent is hereby corrected as shown below:

Column 5, line 28, change "25" to --G 25--.

Column 5, line 57, change "sephadex38" to --Sephadex--.

On the title page, after item [76] Inventors: insert the following:

--[73] Assignee: Novo Nordisk A/S, Gentofte, Denmark--.

Signed and Sealed this

Ninth Day of November, 1993

Attest:

BRUCE LEHMAN

*Attesting Officer*    *Commissioner of Patents and Trademarks*